United States Patent
Deyanov

(10) Patent No.: US 11,089,953 B2
(45) Date of Patent: *Aug. 17, 2021

(54) ENDOSCOPIC INSTRUMENT WITH COMPLIANT THERMAL INTERFACE

(71) Applicant: INTUITIVE SURGICAL OPERATIONS, INC., Sunnyvale, CA (US)

(72) Inventor: Rumen Deyanov, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/881,433

(22) Filed: May 22, 2020

(65) Prior Publication Data

US 2020/0352427 A1    Nov. 12, 2020

Related U.S. Application Data

(63) Continuation of application No. 15/456,947, filed on Mar. 13, 2017, now Pat. No. 10,702,137.

(60) Provisional application No. 62/308,006, filed on Mar. 14, 2016.

(51) Int. Cl.
| | |
|---|---|
| *A61B 1/12* | (2006.01) |
| *A61B 1/00* | (2006.01) |
| *A61B 8/00* | (2006.01) |
| *A61B 8/12* | (2006.01) |
| *A61B 1/012* | (2006.01) |

(52) U.S. Cl.
CPC .......... *A61B 1/128* (2013.01); *A61B 1/00071* (2013.01); *A61B 1/0008* (2013.01); *A61B 1/012* (2013.01); *A61B 1/121* (2013.01); *A61B 8/12* (2013.01); *A61B 8/4483* (2013.01)

(58) Field of Classification Search
CPC ... A61B 1/0076; A61B 1/128; A61B 1/00071; A61B 1/121; A61B 1/0008; A61B 1/012; A61B 1/05; A61B 8/12; A61B 8/4483; H04N 2005/2255
USPC ....................................................... 600/133
See application file for complete search history.

(56) References Cited

U.S. PATENT DOCUMENTS

| | | | |
|---|---|---|---|
| 4,462,462 | A | 7/1984 | Meagher et al. |
| 4,887,154 | A | 12/1989 | Wawro et al. |
| 5,371,753 | A | 12/1994 | Adsett |
| 5,609,561 | A | 3/1997 | Uehara et al. |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — John P Leubecker
(74) *Attorney, Agent, or Firm* — Haynes and Boone, LLP

(57) ABSTRACT

A surgical instrument comprises a heat generating component, a heat sink, an elongate shaft extending from the heat generating component to the heat sink, and an elongate thermal conduit extending within the elongate shaft between the heat generating component and the heat sink. The surgical instrument also comprises a movable contact structure thermally coupled between the elongate thermal conduit and the heat generating component. The elongate thermal conduit extends into the movable contact structure and the movable contact structure is movable relative to the heat generating component.

20 Claims, 4 Drawing Sheets

(56) References Cited

U.S. PATENT DOCUMENTS

| | | | |
|---|---|---|---|
| 6,086,528 | A | 7/2000 | Adair |
| 10,702,137 | B2 * | 7/2020 | Deyanov ................ A61B 1/128 |
| 2004/0207985 | A1 | 10/2004 | Delano et al. |
| 2007/0030656 | A1 | 2/2007 | Ross et al. |
| 2008/0128740 | A1 | 6/2008 | Yamashita et al. |
| 2008/0151046 | A1 | 6/2008 | Scott et al. |
| 2008/0208006 | A1 | 8/2008 | Farr |
| 2011/0306834 | A1 | 12/2011 | Schrader et al. |
| 2015/0335233 | A1 | 11/2015 | Pilz et al. |
| 2017/0258309 | A1 | 9/2017 | Deyanov |

* cited by examiner

ENDOSCOPIC INSTRUMENT WITH COMPLIANT THERMAL INTERFACE

RELATED APPLICATIONS

This application is a continuation of U.S. patent application Ser. No. 15/456,947 filed Mar. 13, 2017 entitled "ENDOSCOPIC INSTRUMENT WITH COMPLIANT THERMAL INTERFACE," issued as U.S. Pat. No. 10,702,137 which claims priority to U.S. provisional patent application 62/308,006, filed on Mar. 14, 2016, both of which are incorporated herein by reference in their entirety.

FIELD

The present disclosure is directed to an endoscopic instrument that includes a heat transfer element that accommodates differential thermal expansion/contraction of the instrument structure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Such endoscopic tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Endoscopic instruments are typically intended to be used for multiple procedures, and so must be cleaned and sterilized between such procedures. A common sterilization method is the use of autoclaving to apply elevated temperatures and pressures to used instruments to destroy or inactivate bacteria, viruses, and other contaminants that might be found on such instruments. However, some endoscopic instruments can have difficulty surviving such high-temperature environments due to the differing coefficients of thermal expansion of the various components making up such instruments Instruments that include dedicated cooling structures can be particularly susceptible to such thermal mismatch issues, as the cooling structures are specifically designed or selected to have specific thermal properties that differ from that of the surrounding instrument structure. For example, endoscopes having distal digital imaging sensors can incorporate heat pipes or other thermal conduits to ensure that the heat generated by such imaging sensors are shunted away to prevent damage to the sensors and/or injury to the patient. However, although rigidly fixing the heat pipe to the imaging sensor and some remote heat sink in the endoscope can provide the desired intraoperative image sensor cooling, the post-operative autoclaving of an endoscope with such a construction can be problematic because the heat pipe and the surrounding endoscope structure will exhibit different dimensional changes in response to the elevated thermal load, which in turn can lead to physical failure of the heat pipe and/or its thermal connections.

Accordingly, it is desirable to provide an endoscopic instrument that incorporates thermal management structures capable of surviving large temperature changes in the instrument.

SUMMARY

By incorporating a movable contact structure between a thermal conduit and heat sink in an endoscopic instrument, elevated temperatures such as in an autoclave can be applied to the instrument without damaging the thermal connection between the thermal conduit and the heat sink.

In various embodiments, an endoscopic instrument includes a heat-generating component that is thermally coupled to a heat sink via a movable contact structure. The heat-generating component can be any element requiring cooling during use, such as an image sensor/processor, electrode, illumination source, laser diode, ultrasound transducer, or data processing node, among others. The thermal conduit can be any structure capable of providing a thermal path between its ends, such as a metallic rod, a heat pipe, or a thermal strap, among others.

The movable contact structure accommodates the relative motion between the thermal conduit and heat sink to maintain the thermal coupling between those elements, such as providing sliding or rolling contact, or providing a flexible coupling, between the thermal conduit and the heat sink. In various other embodiments, the movable contact structure can provide such relative motion accommodation between the heat-generating component and the thermal conduit.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

Figure 1A:
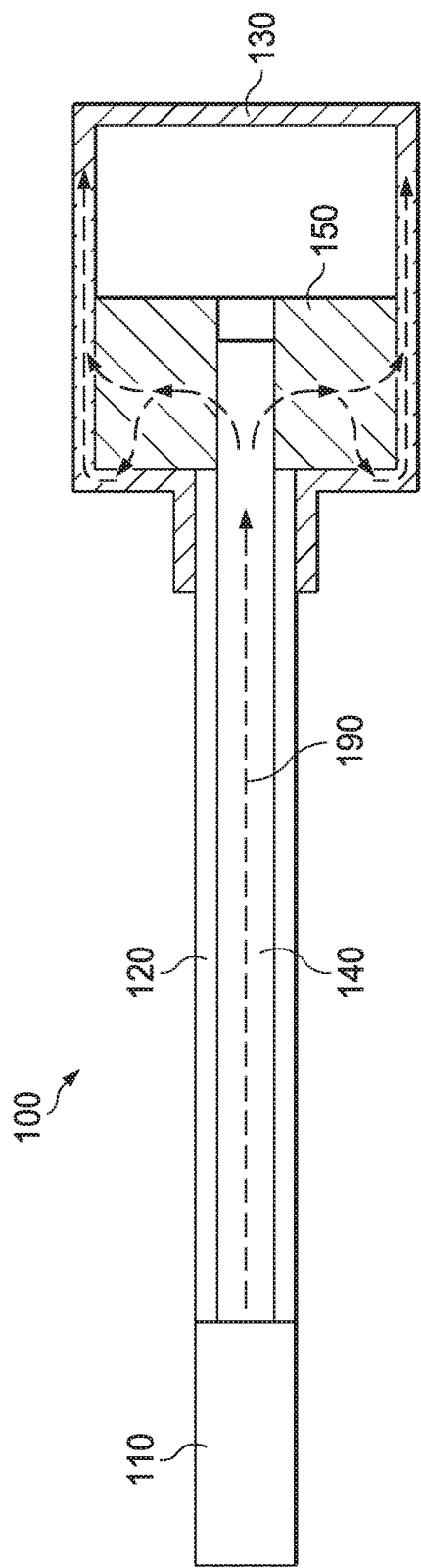
FIGS. 1A and 1B show an exemplary endoscopic instrument that includes a heat generating component, a thermal conduit for the heat generating component, a heat sink, and a movable contact structure for maintaining thermal contact between the thermal conduit and the heat sink.

FIG. 1A shows an endoscopic instrument 100 (also referred to as "endoscope 100") that includes a heat-generating component 110, an elongate shaft physically coupling component 110 to a heat sink 130, a thermal conduit 140 in thermal contact with component 110, and a movable contact structure 150 that thermally couples component 110 to heat sink 130. Heat generated at component 110 is thus transferred via thermal conduit 140 to movable contact structure 150, and then out through heat sink 130, as indicated by the dashed arrows 190. In various embodiments, heat sink 130 can be anything from a dedicated thermal sink in instrument 100 to the body of instrument 100.

Heat-generating component 110 can be any element within an endoscopic instrument that generates heat that must be actively removed during use, such as an image sensor/processor, electrode, illumination source, laser diode, ultrasound transducer, or data processing element, among others. Likewise, thermal conduit 140 can be any thermal conduit capable of providing a thermal path between its ends, such as a metallic rod, a heat pipe, or a thermal strap, among others. Finally, although depicted as a straight element for exemplary purposes, in various embodiments shaft 120 can be bent, curved, flexible, or steerable.

Figure 1B:
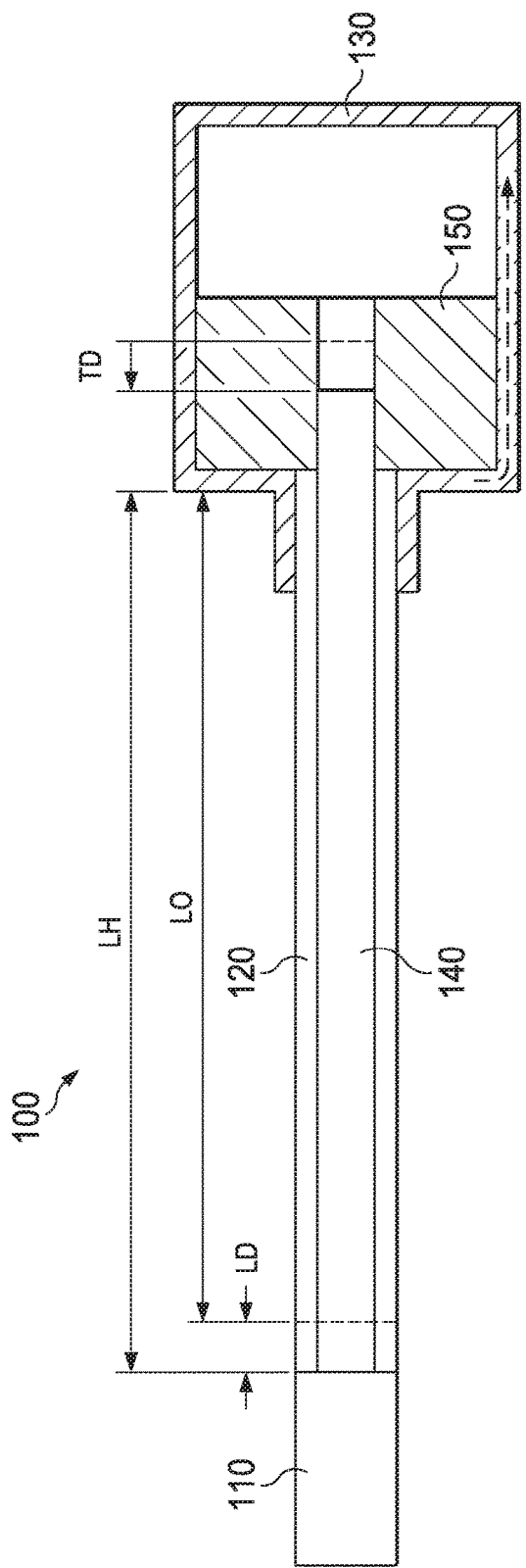

During autoclaving, endoscope 100 is exposed to a high temperature environment that causes shaft 120 to lengthen, moving heat-generating component 110 from its original distance LO from heat sink 130, to an increased distance LH from heat sink 130, as shown in FIG. 1B. Typically, thermal conduit 140 will have a different coefficient of thermal expansion than shaft 120, and therefore if thermal conduit 140 is rigidly connected to heat-generating component 110, the lengthening of shaft 120 will move thermal conduit 140 relative to heat sink 130, as indicated by differential distance TD. Movable contact structure 150 accommodates this relative motion, thereby preventing destruction of the thermal path between thermal conduit 140 and heat sink 130 during autoclaving.

Note that while movable contact structure 150 is depicted and described as being disposed between thermal conduit 140 and heat sink 130 (thereby allowing thermal conduit 140 to be fixed to heat-generating component 110) for exemplary purposes, in various other embodiments movable contact structure 150 could alternative or additionally be disposed between heat-generating component 110 and thermal conduit 140. Although in general there would be less size restrictions at the heat sink region of an endoscopic instrument, allowing for simpler incorporation of movable contact structure 150 at such region, in various embodiments it could be beneficial to provide movable contact structure 150 in the vicinity of heat-generating component 110 (for example, if the region directly around heat-generating component 110 includes a much greater expected differential in thermal expansion).

Movable contact structure 150 can accommodate the relative motion between thermal conduit 140 and heat sink 130 in any manner that maintains the thermal coupling between those elements, such as providing sliding or rolling contact at interface between thermal conduit 140 and movable contact structure 150 and/or between movable contact structure 150 and heat sink 130, or providing a flexible coupling between thermal conduit 140 and heat sink 130 (e.g., via flexible thermally conductive structures or materials), among others.

Figure 2A:
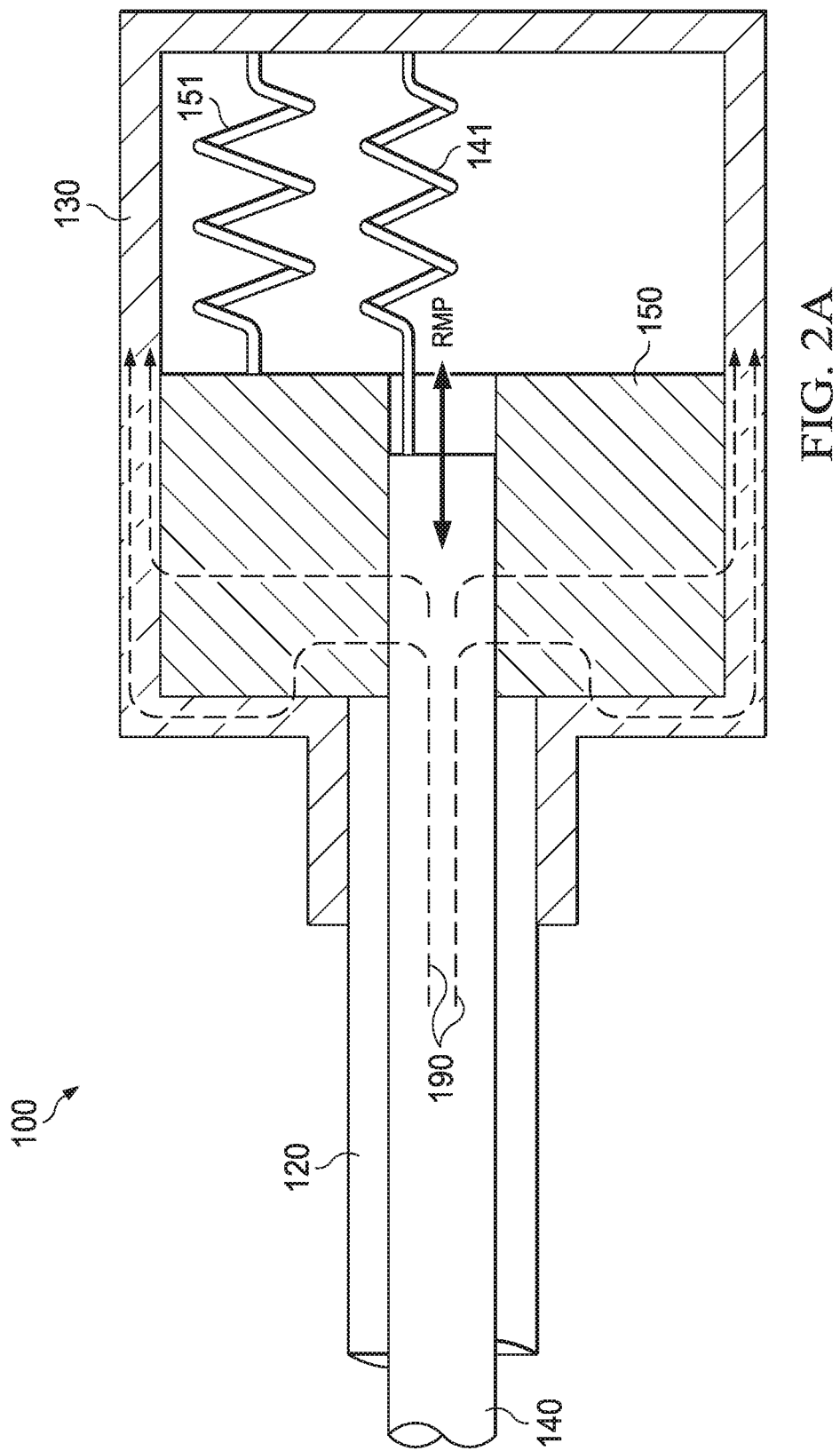
FIGS. 2A-2C show exemplary movable contact structures that could be incorporated into the endoscopic instrument of FIGS. 1A and 1B.

FIG. 2A shows an embodiment of movable contact structure 150, in which thermal conduit 140 is in sliding contact with movable contact structure 150. Movable contact structure 150 remains in contact with heat sink 130, thereby maintaining a thermal path (indicated by the dashed arrows 190) between thermal conduit 140 and heat sink 130, even as thermal conduit 140 slides within movable contact structure 150. In various embodiments, a thermally conductive lubricant (e.g., thermal grease) can be used between thermal conduit 140 and movable contact structure 150 to enhance thermal transfer properties. In this manner, the lengthening of shaft 120 during autoclaving of instrument 100 does not break the thermal path.

In various embodiments, movable contact structure 150 and/or thermal conduit 140 can be biased in a desired direction by optional springs 151 and 141, respectively, to maintain a consistent baseline configuration even after thermal cycling of instrument 100. For example, optional spring 141 can bias thermal conduit 140 towards heat-generating component 110 (not shown) to ensure that thermal conduit 140 is not pulled away from heat-generating component 110 during post-autoclaving cool down of instrument 100.

Figure 2B:
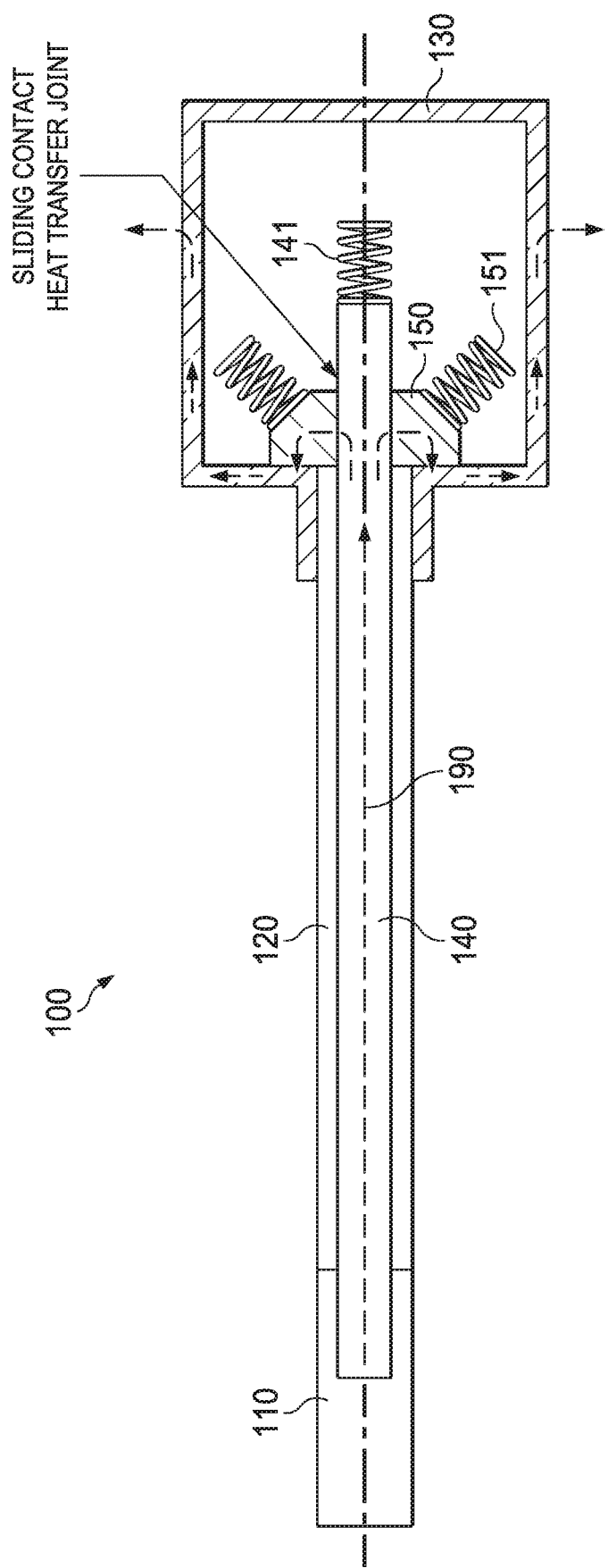

FIG. 2B shows another embodiment of instrument 100 in which thermal conduit 140 is in sliding contact with movable contact structure 150. Movable contact structure 150 is biased against heat sink 130 by springs 151 to maintain thermal contact, while thermal conduit 140 is biased towards heat-generating component 110 by spring 141 to maintain a resilient construction that accommodates the different rates of thermal expansion exhibited by shaft 120 and thermal conduit 140 during autoclaving.

Figure 2C:
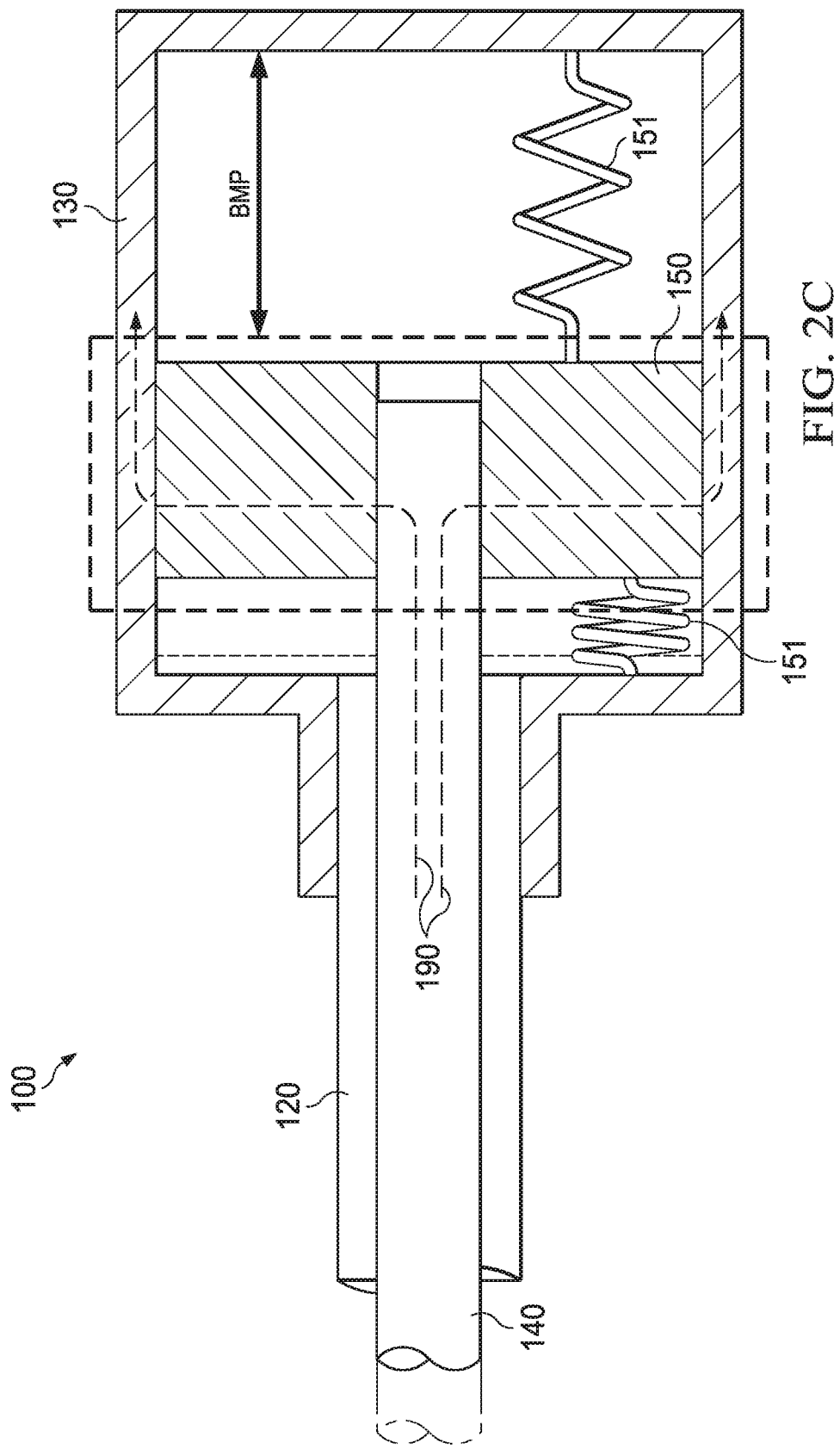

FIG. 2C shows another embodiment of movable contact structure 150, in which thermal conduit 140 is fixed to movable contact structure 150, but movable contact structure 150 is in sliding contact with heat sink 130. Therefore, during expansion of shaft 120 during autoclaving, movable contact structure 150 slides with respect to heat sink 130 to accommodate the difference in coefficients of thermal expansion. In various embodiments, a thermally conductive lubricant (e.g., thermal grease) can be used between movable contact structure 150 and heat sink 130 to enhance thermal transfer properties. In various other embodiments, optional springs 151 can be incorporated to bias movable contact structure 150 towards and/or away from a desired baseline position with heat sink 130.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A surgical instrument comprising:
   a heat generating component;
   a heat sink;
   an elongate shaft extending from the heat generating component to the heat sink;
   an elongate thermal conduit extending within the elongate shaft between the heat generating component and the heat sink; and a movable contact structure thermally coupled between the elongate thermal conduit and the heat generating component, wherein the elongate thermal conduit extends into the movable contact structure and the movable contact structure is movable relative to the heat generating component.

2. The surgical instrument of claim 1, wherein the heat generating component comprises at least one of an image sensor, an image processor, an electrode, an illumination source, a laser diode, an ultrasound transducer, and a data processing element.

3. The surgical instrument of claim 1, wherein the elongate thermal conduit comprises at least one of a metallic rod, a heat pipe, and a thermal strap.

4. The surgical instrument of claim 1, further comprising a spring for biasing the elongate thermal conduit towards the heat generating component.

5. The surgical instrument of claim 1, further comprising a spring for biasing the movable contact structure towards a baseline position relative to the heat generating component.

6. The surgical instrument of claim 5, further comprising a second spring for biasing the elongate thermal conduit towards the heat sink.

7. The surgical instrument of claim 1, wherein the surgical instrument comprises an endoscope.

8. The surgical instrument of claim 1, wherein the elongate shaft is rigid.

9. The surgical instrument of claim 1, wherein the elongate shaft is flexible.

10. The surgical instrument of claim 1, wherein the elongate shaft is steerable.

11. An endoscopic instrument comprising:
a heat generating component;
a heat sink;
an elongate shaft extending from the heat generating component to the heat sink;
a thermal conduit coupled to the heat sink and disposed at least partially within the elongate shaft, the thermal conduit having a coefficient of thermal expansion different than that of the elongate shaft;
a movable contact structure positioned within the heat generating component and thermally coupled between the thermal conduit and the heat generating component, wherein the movable contact structure is configured to accommodate relative motion between at least one of the heat generating component and the thermal conduit or the thermal conduit and the heat sink; and
at least one spring to bias at least one of the thermal conduit or the movable contact structure to maintain thermal coupling between the movable contact structure and the thermal conduit.

12. The endoscopic instrument of claim 11,
wherein the thermal conduit is fixedly coupled to the heat sink, and
wherein the movable contact structure provides movable thermal coupling between the thermal conduit and the heat generating component.

13. The endoscopic instrument of claim 11,
wherein the thermal conduit is movably coupled to the heat sink, and
wherein the movable contact structure provides movable thermal coupling between the thermal conduit and the heat generating component.

14. The endoscopic instrument of claim 11, further comprising:
a second contact structure providing movable thermal coupling between the thermal conduit and the heat sink.

15. The endoscopic instrument of claim 11, wherein the heat generating component comprises at least one of an image sensor, an image processor, an electrode, an illumination source, a laser diode, an ultrasound transducer, and a data processing element.

16. The endoscopic instrument of claim 11, wherein the thermal conduit comprises at least one of a metallic rod, a heat pipe, and a thermal strap.

17. The endoscopic instrument of claim 11, wherein the endoscopic instrument comprises an endoscope.

18. The endoscopic instrument of claim 11, wherein the elongate shaft is rigid.

19. The endoscopic instrument of claim 11, wherein the elongate shaft is flexible.

20. An endoscopic instrument comprising:
a heat generating component;
a heat sink;
a steerable elongate shaft extending between the heat generating component and the heat sink;
a thermal conduit thermally coupled to the heat generating component and disposed at least partially within the elongate shaft, the thermal conduit having a coefficient of thermal expansion different than that of the elongate shaft;
a movable contact structure thermally coupled between the thermal conduit and the heat generating component, wherein the movable contact structure is configured to accommodate relative motion between at least one of the heat generating component and the thermal conduit or the thermal conduit and the heat sink; and
at least one spring to bias at least one of the thermal conduit or the movable contact structure to maintain thermal coupling between the heat generating component and the thermal conduit.

* * * * *